US006735331B1

(12) United States Patent
Binnun et al.

(10) Patent No.: US 6,735,331 B1
(45) Date of Patent: May 11, 2004

(54) METHOD AND APPARATUS FOR EARLY DETECTION AND CLASSIFICATION OF RETINAL PATHOLOGIES

(75) Inventors: Emanuel Binnun, Jerusalem (IL); Avner Karpol, Nos Ziona (IL)

(73) Assignee: Talia Technology Ltd., Neve Ilan (IL)

( * ) Notice: Subject to any disclaimer, the term of this patent is extended or adjusted under 35 U.S.C. 154(b) by 562 days.

(21) Appl. No.: 09/655,371

(22) Filed: Sep. 5, 2000

(51) Int. Cl.[7] ................................................. G06K 9/00
(52) U.S. Cl. ....................... 382/133; 351/206; 600/402; 382/154
(58) Field of Search ................................ 382/128, 127, 382/129, 130, 133, 134, 132, 154; 514/913, 914, 206, 221, 68, 78, 912, 63; 424/78.04, 93.21; 356/456, 632; 351/221, 206, 402; 600/408, 407, 476; 430/30

(56) References Cited

U.S. PATENT DOCUMENTS

| | | | | |
|---|---|---|---|---|
| 5,303,709 A | * | 4/1994 | Dreher et al. ............... | 600/476 |
| 5,776,063 A | * | 7/1998 | Dittrich et al. .............. | 600/408 |
| 6,267,477 B1 | * | 7/2001 | Karpol et al. ............... | 351/221 |
| 6,268,093 B1 | * | 7/2001 | Kenan et al. ................ | 430/30 |
| 6,276,798 B1 | * | 8/2001 | Gil et al. .................... | 351/206 |
| 6,440,950 B1 | * | 8/2002 | Zeimer ........................ | 514/63 |
| 6,556,853 B1 | * | 4/2003 | Cabib et al. ................ | 600/407 |

OTHER PUBLICATIONS

"Quantitative Reflectometry of the Ocular Fundus", by Robert W. Knighton, 4527 IEEE Engineering in Medicine and Biology 14 (1995) Jan./Feb., No. 1, New York, US, pp. 43–51.

* cited by examiner

Primary Examiner—Timothy M. Johnson
Assistant Examiner—Seyed Azarian
(74) Attorney, Agent, or Firm—Lowe Hauptman Gilman & Berner LLP

(57) ABSTRACT

A method and apparatus for early detection and classification of retinal pathologies, especially glaucoma and macular edema. The method comprises; (a) illuminating predetermined locations on the retina; (b) receiving light returning from predetermined locations; (c) generating a series of primary graphs corresponding to the light intensity with respect to retinal depth of predetermined locations on the retina; (d) separating the component curves of said graphs; (e) analyzing said component curves to produce data including data corresponding to the front slope and/or the back slope, and/or the area of at least one of said component curves; (f) comparing said data to analogous pre-specified data.

16 Claims, 4 Drawing Sheets

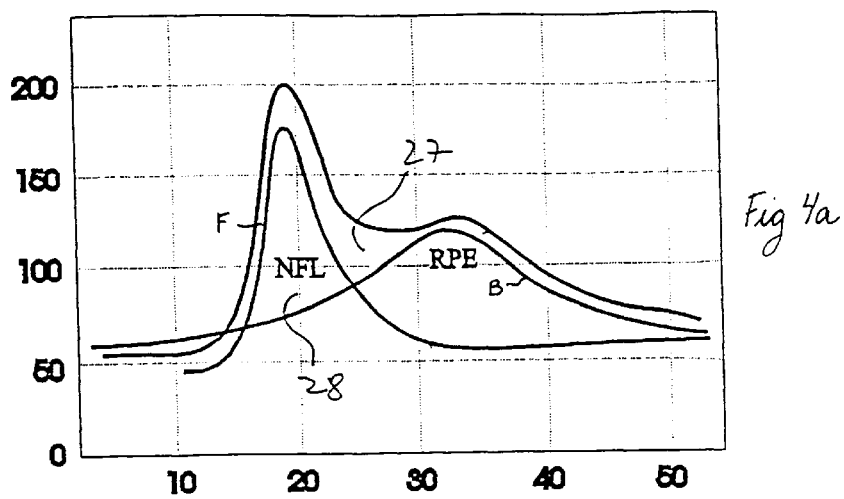
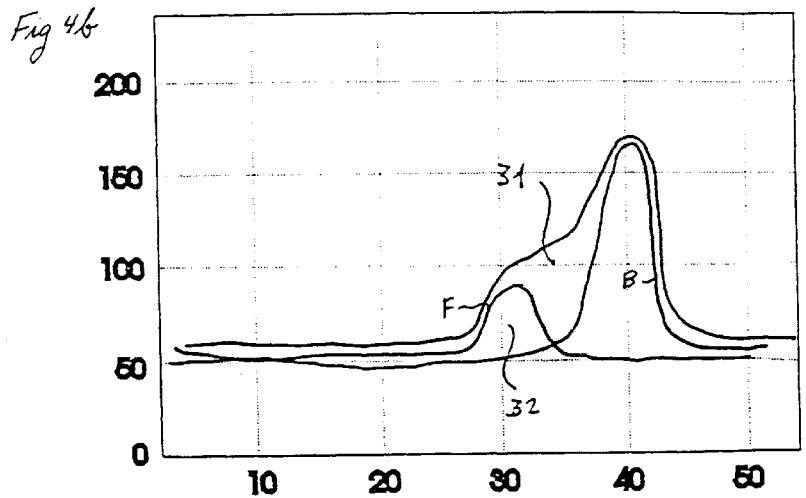
FIGURE 4
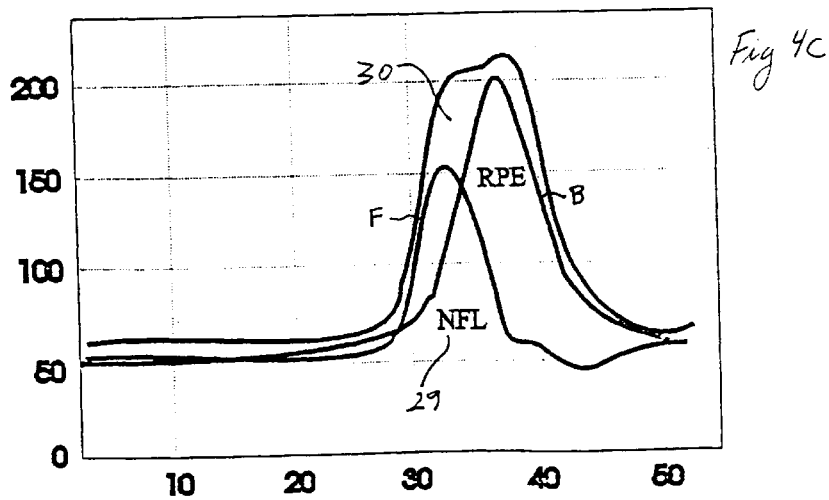

METHOD AND APPARATUS FOR EARLY DETECTION AND CLASSIFICATION OF RETINAL PATHOLOGIES

FIELD OF THE INVENTION

The present invention relates to a method and apparatus for the early detection and classification of retinal pathologies. More specifically, the present invention relates to a method and apparatus for early detection and identification of retinal pathology, including glaucoma and macular edema associated with diabetic retinopathy. In particular, the system of the present invention can be used to measure the relative amount of live fibers in a region of the Nerve Fiber Layer (hereinafter referred to as the "NFL") of the retina to detect glaucoma at its very early stages, the opacification of the retina to detect edema, and changes in optic disk topography to detect the presence and/or progression of glaucoma.

BACKGROUND OF THE INVENTION

Various retinal pathologies are known that can have moderate to severe effects on vision. Chief among them are glaucoma and edema associated with diabetic retinopathy. Glaucoma, characterized by nerve fiber loss (especially in the Nerve Fiber Layer of the retina) and ganglion cell loss, produces a progressive reduction in visual function beginning at the periphery of the field of vision and progressing inwardly to cause "tunnel vision." If left untreated, it can lead to total blindness. Edema, a thickening of the retina (particularly in the macular region), results from leakage of blood vessels and causes a reduction in visual acuity. When a reduction in visual acuity occurs in a patient, it is up to the ophthalmologist to determine where the source of the problem is in the eye so that a suitable treatment can be planned. One way often used to test for the edema is by using flourescein angiography. However, this method is invasive, time-consuming, not quantitative, and the intensity of the fluouscence is not directly related to the edema.

The retina is both thin and transparent, and identification of problems in the retinal layers is difficult. In the case of glaucoma, changes in the retina have traditionally been able to be detected only after irreversible visual loss or damage has occurred. Considering that up to 50% of nerve fibers at a predetermined retinal region may be lost before a detectable vision problem occurs, it would be of significant advantage to be able to identify and quantify retinal changes before visual damage occurs. In particular, it would be of utmost benefit to be able to detect and quantify changes in the NFL (an indicator of glaucoma) and opacification of the retina (an indicator of edema) at a previously unattainable early stage.

One way ophthalmologists can diagnose glaucoma is through the use of Perimetry. Perimetry, however, detects only the functional irreversible damage in the retina that has already resulted in irreversible visual loss and does not detect the preceding physiological changes.

It is therefore the primary object of the present invention to provide a method and apparatus for the early detection and classification of retinal pathologies, including edema and glaucoma. Particularly, it is an object of the present invention to provide an apparatus and method for detecting retinal pathologies by determining and quantifying particular characteristics in the light scattering patterns of the different sublayers and regions of the retina. It is also an object of the present invention to provide an apparatus capable of precisely detecting retinal pathologies that is both noninvasive and capable of detecting problems before visual loss or damage occurs.

These and other objects of the present invention will become more apparent from the summary of the invention and detailed description of the drawings that follows.

SUMMARY OF THE INVENTION

The present invention relates to a method for early detection of retinal pathologies, especially glaucoma and diabetic macular edema. The method comprises the steps of: (a) illuminating a sequence of predetermined locations on the retina; (b) receiving light returning from said predetermined locations on the retina; (c) generating a series of primary graphs corresponding to the light intensity with respect to retinal depth of each of said predetermined locations on the retina; (d) separating the component curves of said primary graphs (one main component curve corresponds to light returning substantially from the Nerve Fiber Layer; a second main component curve corresponds to light returning substantially from the Retinal Pigment Epithelium); (e) analyzing said component curves (according to predetermined algorithms) to obtain data including, but not limited to, data corresponding to the front and/or back slopes and/or the area of at least one of the component curves; (f) comparing said data to analogous pre-specified data (to quantify changes and/or classify pathologies of the retina.)

In a preferred embodiment of the present invention, the method further includes the step of determining the retinal thickness for each of said predetermined locations of the retina, by employing, for example, the calculated distance between the component curves of the primary graph (it is appreciated that other approaches may be appropriately employed for determining retinal thickness.)

It should be appreciated that the sequence of predetermined locations on the retina need not be linearly spaced. Rather, said sequence of predetermined locations may refer to any particular region or area of the retina that may further be divided into sub-regions that are illuminated in a sequential manner (for a predetermined period) for the purpose of obtaining information about the light scattering pattern and/or changes in the light scattering pattern occurring over a region of the retina.

It should also be appreciated that separation of the component curves may be accomplished through any appropriate method such as by using curve-fitting methods including fitting a Lorenzian function of the primary graph and translating the Lorenzian to delineate a component curve corresponding substantially to the light returned from the Retinal Pigment Epithelium according to appropriate Lorenzian tables and, thereafter, subtracting the component curve corresponding to the Retinal Pigment Epithelium from the primary graph to obtain a second component curve corresponding substantially to the light returned from the NFL.

In accordance with a preferred embodiment of the present invention, the method further comprises the step of generating at least one three-dimensional map. Said map may correspond, for example, to the retinal thickness of the sequence of the predetermined locations of the retina. It is appreciated that a three-dimensional map may be generated corresponding to any one or more of the parameters measured (two dimensions corresponding to the position on the retina and one dimension corresponding to the measured parameter value). In one preferred embodiment, the method further comprises the step of generating at least one three-dimensional map representative of the relative amount of cells in the Nerve Fiber Layer of the retina over the sequence of predetermined locations on the retina (this map is preferably generated based on the calculated area of the component curves of the primary graphs that correspond to the NFL).

In further preferred embodiments of the present invention, the data is arranged in a matrix for enabling comparison with pre-specified data that is arranged in an analogous format.

In still further preferred embodiments of the present invention, the data corresponds to the area of the component curve that corresponds to the Nerve Fiber Layer of the retina.

Moreover in accordance with other preferred embodiments of the present invention, the data corresponds to the ratio of the area of the component curve corresponding to the Nerve Fiber Layer to the area of the component curve corresponding to the Retinal Pigment Epithelium.

In another preferred embodiment of the present invention, the data corresponds to the ratio of the area of component curve corresponding to the Nerve Fiber Layer to the area of the primary graph.

Moreover, in another preferred embodiment of the present invention, the data corresponds to differences between the Line Spread Function of the component curve corresponding to the Nerve Fiber Layer and the Line Spread Function of the component curve corresponding to the Retinal Pigment Epithelium. It is appreciated that a comparison between the two Line Spread Functions (LSF's) may include calculation and comparison of a variety of different measurements. In one preferred embodiment, the back slope (i.e., the slope of the descending portion) of the component curve corresponding to the Retinal Pigment Epithelium is compared with the front slope (i.e., the slope of the ascending portion) of the component curve corresponding to the Nerve Fiber Layer.

In one preferred embodiment of the present invention, the pre-specified data is obtained from normal retinas. For example, if the region of the retina being illuminated includes the optic disk, the resultant data can be compared to data obtained from known normal (i.e., healthy) optic disks. In another preferred embodiment of the present invention, the pre-specified data is obtained from an earlier examination of the retina being examined. In another preferred embodiment of the present invention, the pre-specified data contains data obtained from known normal (i.e., healthy) optic disks and from an earlier examination of the retina being examined.

In a preferred embodiment of the present invention, the regions of the retina are illuminated successively according to a predetermined illumination sequence useful for the detection of a specific predetermined retinal region.

The present invention also relates to an apparatus for mapping the inner structure of the retina using the method hereinbefore described, that is especially useful for the early detection of retinal pathologies including glaucoma and diabetic macular edema. The apparatus comprises; (a) illuminating means for illuminating a sequence of predetermined locations on the retina and for receiving light returning from said predetermined locations on the retina; (b) computing means adapted to producing a series of primary graphs corresponding to the light intensity with respect to retinal depth of each of said predetermined locations of the retina, for resolving the component curves of said primary graphs, for analyzing the component curves to obtain data including data corresponding to the front and/or back slopes and/or the area of at least one of said component curves, and for comparing said data to analogous pre-specified data (to quantify changes and classify pathologies in the retina.)

It is appreciated that the illuminating means may be of any appropriate type known in the art for enabling production of optical cross section images from each location of the retina. For example, the illuminating means may comprise an instrument having a helium-neon laser, operating at a length of 543 nm, mounted on a slit-lamp biomicroscope. The expanded laser beam is directed toward the eye by a beam splitter and focused by the objective of the biomicroscope. The image of the intersection of the slit with the retina may be recorded on film via a second objective of the biomicroscope.

BRIEF DESCRIPTION OF THE DRAWINGS

The invention is herein described, by way of example only, with reference to the accompanying drawings, wherein:

FIGS. 4a, 4b, and 4c illustrate three examples of light intensity graphs.

DETAILED DESCRIPTION OF THE DRAWINGS

The present invention be described with reference to FIGS. 1–5. The figures are solely intended to illustrate certain preferred embodiments of the present invention, and in no manner intend to limit the scope of the invention, as set out in the claims.

In a preferred embodiment of the present invention, a helium-neon laser mounted on a slit-lamp biomicroscope is used to direct a laser beam to the eye by a beam splitter and to focus said beam on the fundus by an objective of the biomicroscope to which a cylindrical lens is attached. The laser beam is preferably 20 micrometers wide and 2 millimeters long and directed at a slanted angle to the retina. The image of the intersection of the slit with the retina is photographed via a second objective of the biomicroscope to which a fundus camera is attached.

Figure 1:
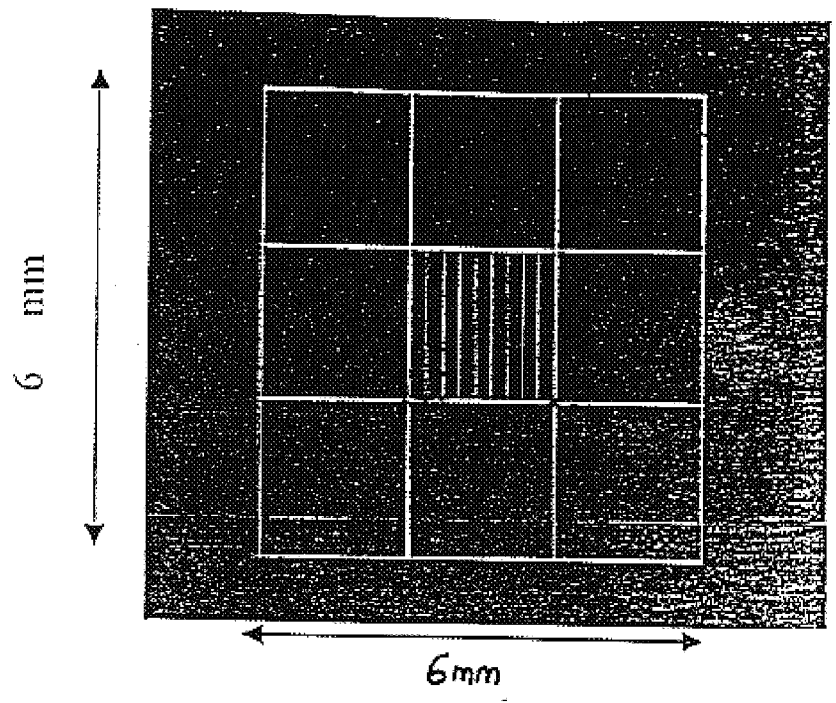
FIG. 1 is an example of the sectioning of a portion the retina by a slit light camera according to the present invention.

Referring now to FIG. 1, and to a preferred embodiment of the present invention, nine scans are performed on a retina such that an area of 6 by 6 millimeters of the retina is covered. Preferably, for each scan, ten slit images are produced within 0.2 seconds (for the sake of clarity, slits are depicted only on the central scan). The slits are spaced at a distance of approximately 200 micrometers from one another on the retina. Each slit has a height of approximately 2 millimeters and a width of approximately 20 micrometers. The area scanned can be localized with the help of a fundus image (seen behind the scan) which is acquired simultaneously with the slit image. It should be appreciated, however, that the individual scan size, the number of slits, and the area covered, may vary according to the degree of detail required and the pathology of the particular retina.

Figure 2:
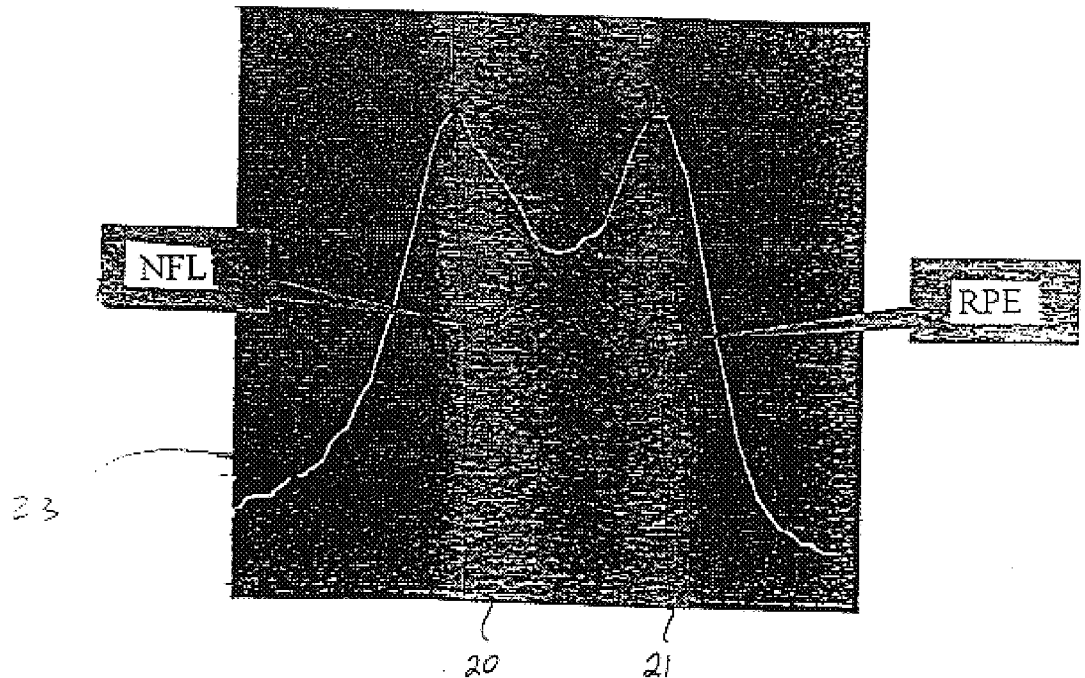
FIG. 2 is shows the light-scattering pattern obtained from a small part of a discrete slit on the retina, overlaid by a computer-generated graph corresponding to the light-intensity of a selected point on the slit.

Referring now to FIG. 2, a light-scattering pattern obtained from a location on the retina contains 2 light-intense regions (20) (21), corresponding to light received substantially from the NFL region, and from light received substantially from the Retinal Pigment Epithelium (hereinafter referred to as the RPE), respectively (it should be appreciated that the light-scattering pattern appears different in regions of the retina such as the optic disk). Each of the regions (20) (21) correspond to a 2 millimeter height on the retina. A graph (23) is generated by the computer of the system. The computer-generated graph (23) provides convenient means for a general examination of the curvature and intensity of each of the light-intense regions. However, the computer-generated graph does not represent only the light returning from the NFL and RPE since light from other layers of the retina also contributes to the graph. The graph (23) represents one of ten similar graphs produced from ten of said predetermined locations spaced vertically along the light intense regions (20) (21).

Figure 3:
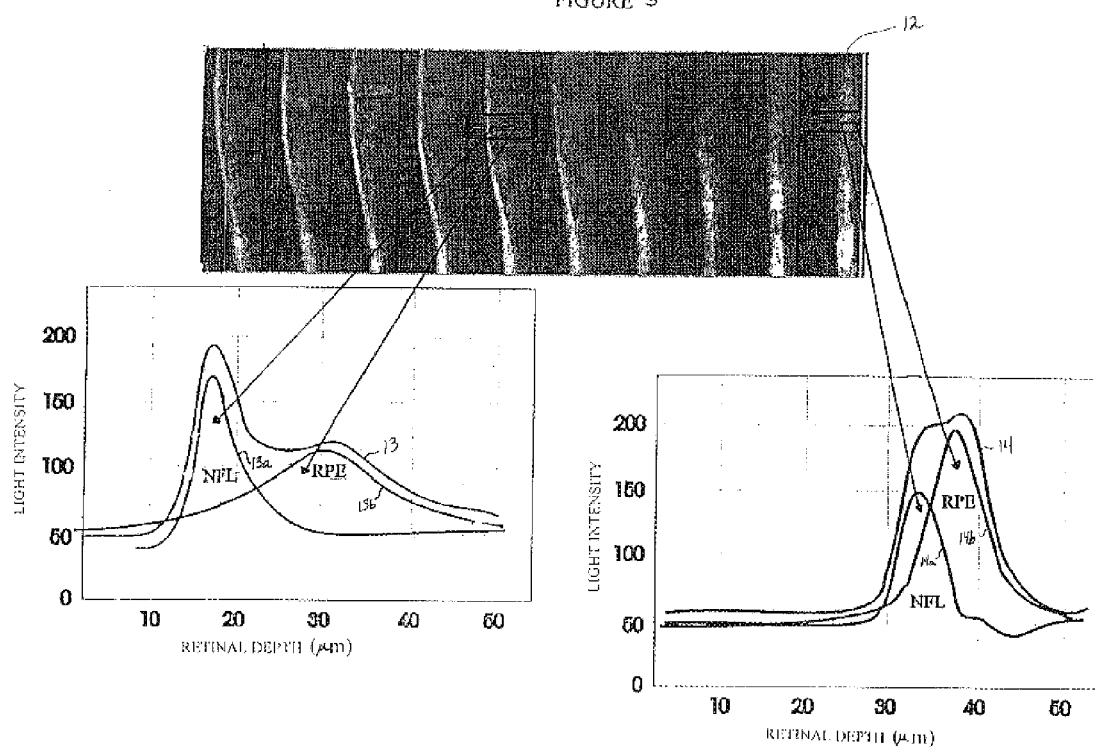
FIG. 3 illustrates a series of returning-light images received from discrete illumination slits on the retina and two light intensity graphs produced from selected points on the returning-light images.

Referring now to FIG. 3, a unique optical cross section (12) is obtained from illumination through each of the aforementioned slits (for the sake of clarity, only one optical cross section (12) is labeled in FIG. 3). Each slit has a height of approximately 2000 microns. To compensate for the angle of incidence onto the retina, the width of each scan is "stretched" using an appropriate correction factor. While the optical cross sections may, by careful examination, reveal various retinal pathologies such as retinal detachments, holes, cysts, etc. such pathologies can be more readily discovered, diagnosed, and quantified by the use of a computer-generated graph (hereinafter referred to as a "light-intensity graph") relating to the light intensity versus retinal depth at any distinct segment in an individual scan. Two such light-intensity graphs (13) (14) are shown in FIG. 3. As mentioned previously, the light-intensity graphs show the combined light-scattering pattern of the retinal layers. Thus, while two prominent light-intense regions are visible in the graph, corresponding to the NFL region and the RPE region, it would nonetheless be advantageous to obtain discrete curves corresponding to light received only from the NFL (13a) (14a) and only from the RPE regions (13b) (14b), respectively, in order to gain an accurate picture of the inner structure of the retina, particularly, the NFL region. In one preferred embodiment of the present invention, the individual components of the light-intensity graphs are resolved using curve-fitting methods, and converted into data corresponding to various characteristics of the component curves. The data can then be arranged in a matrix (according to one preferred embodiment) or any other appropriate chart, graph, or table for comparison to pre-specified data, arranged in an analogous format, for comparison and disclosure of information pertaining to the particular retina. It should be appreciated that numerous data, relating, in particular (though not limited to) the front and back slopes of the NFL and RPE component curves, and the area of the NFL component curve can be constructed and analyzed and further compared to other data. By analyzing the area of the component curve corresponding to the NFL layer, cell loss (if any) in the NFL can be determined and quantified. By comparing the Line Spread Functions of the NFL component curve and the RPE component curve, it can be determined whether (and what portion of) a loss in visual acuity is the result of a retinal abnormality or another abnormality of the eye (for example, a cataract). Said determination may be made, for example, by calculating the difference between the front slope (the ascending slope) of the NFL curve and the back slope (the descending slope) of the RPE curve and by comparing the results with appropriate data.

FIGS. 4a–c illustrates three examples of light-intensity graphs. FIG. 4a illustrates the reflection from a retinal region having a normal NFL region. The total area of the NFL peak (28) is substantially within the range of typical respective areas (approximately 40% of the total area) measured in normal retinas, and the ratio between the total NFL peak area (28) and the actual reflection graph area (27) falls within the normal percentage range. Accordingly, the NFL density and/or width at the region of the retina that was illuminated may be considered normal.

FIG. 4b illustrates a reflection from a retinal region having a deficient NFL region, wherein the respective total NFL peak area (32) is approximately 15% of the primary graph area (31), falling below the normal statistical range (as measured, for example, in normal retinas), thus indicating a reduction in cells in the NFL region. The NFL density and/or width at this region of the retina may be calculated exactly, with reference to pre-specified data tables.

FIG. 4c illustrates another reflection from a retinal region having deficient NFL, wherein the NFL region peak (29) is approximately 30% of the primary graph area, indicating slight abnormalities. The NFL density and/or width at this region of the retina may also be calculated exactly, with reference to pre-specified data tables.

By referring to specific differences between the examples illustrated, another aim of the present invention can be demonstrated. It can be clearly seen that in FIGS. 4b and 4c, the back slope (B) of the intensity graph (relating to light returning from the RPE) is nearly the same (in absolute value) as the front slope (F) of the intensity graph (relating to light returning from the NFL). In the FIG. 4a, however, a significant difference can be observed between the slopes (the front slope (F) is much steeper than the back slope (B)). This is the result of a defect in the transparency of the retina (for example, retinal edema) that causes loss of visual acuity. It can be determined, according to a computational comparison between the front slope (F) and the back slope (B), what percentage of the loss of visual acuity can be attributed to retinal problems, and what percentage can be attributed to problems in other ocular structures (defects in other ocular structures, such as cataracts in the lens of the eye, influence the front and the back slopes in an identical manner, such that any difference in the slopes is necessarily a result of a retinal problem).

Figure 5:
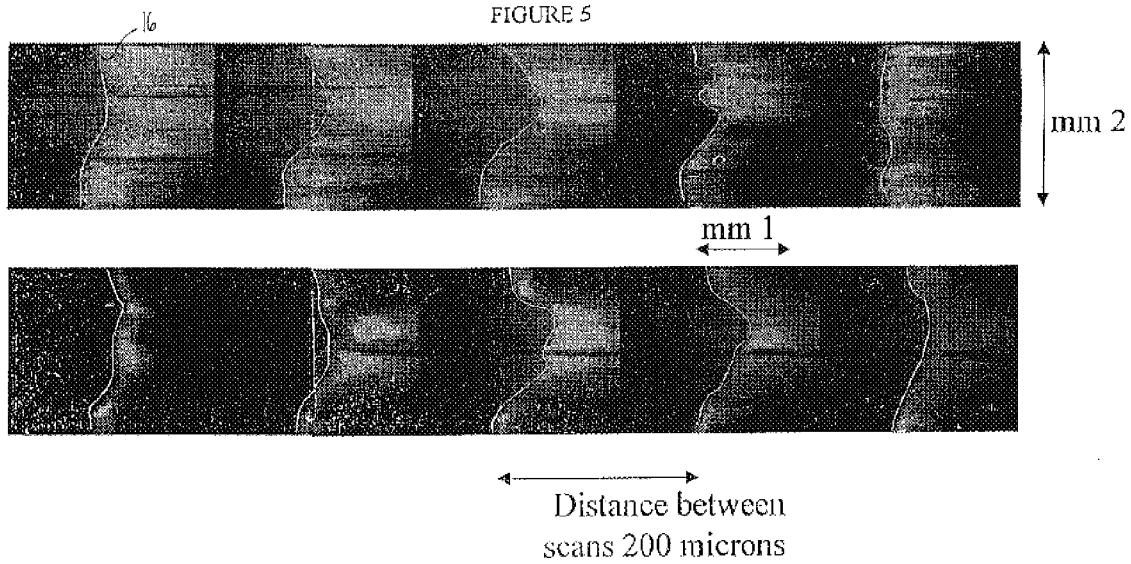
FIG. 5 illustrates a series of returning light images received from discrete illumination slits on an optic nerve head, with computer generated surface profiles.

FIG. 5 illustrates a series of optical cross sections of an optic nerve head, with computer generated surface profiles (16) (for the sake of clarity, only one profile is labeled in FIG. 5). Each step of the scan covers 2 mm height on the retina, and ten scan steps are originated and directed for covering 2 mm laterally on the retina, thus the distance on the retina between two such steps is 200 microns. The optical cross sections acquired from one or more scan sequences can be used to generate a topographical map of the respective optic disk region. The topography and concavity of the optic cross sections can also be analyzed and compared to other data (including data from known healthy retinas or from the same retina at an earlier date) to indicate the loss or progression of the loss of optic nerve fibers.

What is claimed is:

1. A method of detecting and classifying retinal pathologies, including glaucoma and diabetic macular edema, said method comprising:

(a) illuminating a sequence of predetermined locations on a retina;

(b) receiving light returning from said predetermined locations;

(c) generating a series of primary graphs each representing the intensity of the returning light as a function of the retinal depth at one of said predetermined locations;

(d) separating each of said primary graphs into a first component curve corresponding to the light returning substantially from the Nerve Fiber Layer of the retina and a second component curve corresponding to the light returning substantially from the Retinal Pigment Epithelium of the retina;

(e) analyzing at least one of said component curves to obtain data including, but not limited to, data corresponding to the front slope and/or back slope and/or area of said at least one of said component curves; and (f) comparing the data to analogous pre-specified data.

2. A method according to claim 1, further comprising determining the retinal thickness at each of said predetermined locations.

3. A method according to claim 1, wherein the data is arranged in a matrix for enabling comparison with the pre-specified data arranged in an analogous format.

4. A method according to claim 1, further comprising generating at least one three-dimensional map.

5. A method according to claim 1, further comprising generating at least one three-dimensional map corresponding to the relative amount of cells in the Nerve Fiber Layer of the retina over the sequence of said predetermined locations.

6. A method according to claim 1, wherein the data corresponds to the area of the first component curve that corresponds to the Nerve Fiber Layer of the retina.

7. A method according to claim 1, wherein the data corresponds to the ratio of the area of the first component curve corresponds to the Nerve Fiber Layer to the area of the second component curve corresponding to the Retinal Pigment Epithelium.

8. A method according to claim 1, wherein the data corresponds to the ratio of the area of the first component curve corresponding to the Nerve Fiber Layer to the area of the respective primary graph.

9. A method according to claim 1, wherein the data corresponds to differences between the Line Spread Function of the first component curve corresponding to the Nerve Fiber Layer and the Line Spread Function of the second component curve corresponding to the Retinal Pigment Epithelium.

10. A method according to claim 9, wherein the comparison between the Line Spread Functions includes comparing the slope of a rear, descending portion of the second component curve corresponding to the Retinal pigment epithelium with the slope of a front, ascending, portion of the first component curve corresponding to the Nerve Fiber Layer.

11. A method according to claim 1, wherein the data corresponds to the slope of a rear, descending portion of the second component curve corresponding to the Retinal pigment epithelium.

12. A method according to claim 1, wherein the pre-specified data is obtained from normal retinas.

13. A method according to claim 1, wherein the pre-specified data is obtained from an earlier examination of the retina being examined.

14. A method according to claim 1, wherein the regions of the retina are illuminated successively according to a predetermined illumination sequence useful for the detection of a specific retinal region.

15. An apparatus for mapping the inner structure of a retina and for use in early detection of retinal pathologies, including glaucoma and diabetic macular edema, said apparatus comprising:

illuminating means for illuminating a sequence of predetermined locations on the retina and for receiving light returning from said predetermined locations; and computing means for producing a series of primary graphs each representing the intensity of the returning light as a function of the retinal depth at one of said predetermined locations, for separating each of said primary graphs into a first component curve corresponding to the light returning substantially from the Nerve Fiber Layer of the retina and a second component curve corresponding to the light returning substantially from the Retinal Pigment Epithelium of the retina, for analyzing the component curves to obtain data corresponding to at least one of the front slope, the back slope and the area of at least one of said primary curves and component curves, and for comparing said data to analogous pre-specified data to quantify changes in the retina.

16. A method of detecting and classifying retinal pathologies, including glaucoma and diabetic macular edema, said method comprising:

(a) illuminating at least a region of a retina;

(b) receiving, light returning from said region;

(c) representing the intensity of a first component of the returning light, which first component returns substantially from the Nerve Fiber Layer in said region of the retina, as a first function of the retinal depth in said region;

(d) representing the intensity of a second component of the returning light, which second component returns substantially from the Retinal Pigment Epithelium in said region of the retina, as a second function of the retinal depth in said region;

(e) analyzing at least one of said first and second functions to obtain data relating to said at least one of said functions; and (f) comparing the obtained data to pre-specified data.

\* \* \* \* \*